US009304230B2

United States Patent
Pugh et al.

(10) Patent No.: US 9,304,230 B2
(45) Date of Patent: Apr. 5, 2016

(54) HYDROGEL LENS INCLUDING A REMOVABLE MEDIA INSERT

(71) Applicant: Johnson & Johnson Vision Care, Inc., Jacksonville, FL (US)

(72) Inventors: Randall B. Pugh, St. Johns, FL (US); James Daniel Riall, St. Johns, FL (US); Frederick A. Flitsch, New Windsor, NY (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 76 days.

(21) Appl. No.: 13/838,194

(22) Filed: Mar. 15, 2013

(65) Prior Publication Data

US 2014/0268027 A1 Sep. 18, 2014

(51) Int. Cl.
G02C 7/04 (2006.01)
G02B 1/04 (2006.01)
B29D 11/00 (2006.01)
G02C 7/08 (2006.01)
A61F 9/00 (2006.01)

(52) U.S. Cl.
CPC .......... G02B 1/043 (2013.01); B29D 11/00038 (2013.01); B29D 11/00807 (2013.01); G02C 7/04 (2013.01); G02C 7/049 (2013.01); G02C 7/083 (2013.01); A61F 9/0017 (2013.01)

(58) Field of Classification Search
CPC ................................. G02C 7/04; G02C 7/049
USPC ................ 351/159.02, 159.03, 159.33, 159.7
See application file for complete search history.

(56) References Cited

U.S. PATENT DOCUMENTS

| 3,973,837 | A | * | 8/1976 | Page ........................ 351/159.33 |
| 5,044,742 | A | | 9/1991 | Cohen |
| 6,570,386 | B2 | * | 5/2003 | Goldstein ..................... 324/415 |
| 6,576,013 | B1 | | 6/2003 | Budman et al. |
| 8,216,306 | B2 | * | 7/2012 | Coroneo ..................... 623/6.22 |
| 2003/0020477 | A1 | | 1/2003 | Goldstein |
| 2009/0244477 | A1 | * | 10/2009 | Pugh et al. .................... 351/158 |
| 2010/0109175 | A1 | | 5/2010 | Pugh et al. |
| 2012/0092612 | A1 | | 4/2012 | Binder |
| 2014/0085602 | A1 | * | 3/2014 | Ho et al. .................. 351/159.03 |

FOREIGN PATENT DOCUMENTS

WO    WO 2010051203 A1    5/2010

OTHER PUBLICATIONS

EP Search Report Application No. EP 14 15 9733 Dated Jun. 17, 2014.
SG Search Report Application No. 10201400546Y Date of Submission of Search Report Sep. 24, 2014; Date of completion of Search Report Feb. 16, 2015; Date of mailing from Singapore Agent to Johnson & Johnson of Search Report Apr. 20 2015.

* cited by examiner

*Primary Examiner* — Darryl J Collins

(57) ABSTRACT

An ophthalmic device includes a hydrogel lens and a media insert removably attached to the hydrogel lens. A method for removably attaching the media insert to the hydrogel lens includes receiving a first hydrogel lens including an annular opening, at least partially inserting a media insert into the annular opening of the first hydrogel lens, removing the media insert from the annular opening of the first hydrogel lens, receiving a second hydrogel lens including an annular opening, and at least partially inserting the removed media insert into the annular opening of the second hydrogel lens.

18 Claims, 7 Drawing Sheets

HYDROGEL LENS INCLUDING A REMOVABLE MEDIA INSERT

TECHNICAL FIELD

The disclosure generally relates to an ophthalmic device and, more particularly, relates to a hydrogel lens including a removable media insert.

BACKGROUND

Traditionally, ophthalmic devices, such as a hydrogel lens, an intraocular lens or a punctal plug, include corrective, cosmetic or therapeutic qualities. A contact lens, for example, may provide vision correcting functionality, cosmetic enhancement, and/or therapeutic effects. Each function is provided by a physical characteristic of the contact lens. For example, a refractive quality may provide a vision corrective function, a pigment may provide a cosmetic enhancement, and an active agent may provide a therapeutic functionality. Such physical characteristics are accomplished without the lens entering into an energized state.

More recently, it has been theorized that active components, such as semiconductor devices, may be incorporated into a contact lens. However, the topology and size defined by the contact lens structure creates a novel and challenging environment for the definition of components and compositions that are capable of performing various functionalities. For example, it is critical that a contact lens including semiconductor devices be biocompatible and not cause damage to surrounding ocular tissue nor inhibit ocular fluid generation or flow. In particular, it is critical that a sufficient amount of oxygen is able to reach the cornea while the contact lens including semiconductor devices is worn, otherwise eye health may be negatively impacted. For example, an inadequate supply of oxygen to the cornea can result in edema or swelling, hypoxia, and can generally cause a great deal of discomfort which limits the period of time that the contact lens can be worn.

In general, during contact lens wear, oxygen can reach the cornea either by diffusion through the lens material or by freshly oxygenated tear fluid being generated by the eye under the lens during lens motion as the lens is worn. However, some contact lenses may include components or formulations that are made of materials that have low oxygen permeability and, therefore, most of the oxygen reaching the cornea is limited to oxygen from tear mixing.

Consequently, hydrogel lenses are usually preferred over other contact lens materials because they are more comfortable and allow for more oxygen to reach the eye. When a hydrogel contact lens is worn, some oxygen reaches the cornea directly by diffusion through the lens. The amount of oxygen delivered to the cornea through the lens is dependent on the oxygen permeability of the lens. As a hydrogel contact lens is repeatedly worn, however, its oxygen permeable pores can become clogged and the hydrogel material can degrade. Therefore, the oxygen permeability of the hydrogel lens is reduced over time.

As a result of the reduced oxygen permeability and resulting increased risk of damage to the cornea, temporary or disposable hydrogel contact lenses that are disposed following a particular usage time, such as two weeks, as used. However, active components may be relatively costly and, thus, may not be incorporated in disposable hydrogel lenses.

Therefore, there is a need for a hydrogel lens including a removable media insert, where the media insert is configured to be removed from a one hydrogel lens and be removably attached to another hydrogel lens to allow the incorporation of the active components in multiple hydrogel lenses.

SUMMARY

Accordingly, the foregoing needs are met, to a great extent, by one or more embodiments of the hydrogel lens including the removable media insert. In accordance with some embodiments, an ophthalmic device includes a hydrogel lens and a media insert removably attached to the hydrogel lens. The hydrogel lens can include an optic zone and a peripheral zone that is outside of the optic zone. The media insert can be removably attached within the optic zone of the hydrogel lens. Two or more raised portions can be included in the peripheral zone of the hydrogel lens. Gap portions can be located in between the two or more raised portions in the peripheral zone of the hydrogel lens and allow for oxygen transmission and tear flow.

In some embodiments, an upper surface of the media insert may partially protrude from an outer surface of the hydrogel lens. The media insert can include ribs at least partially along its circumference or two or more tabs along its circumference. The tabs can be made of a resilient material.

In some embodiments, the media insert can include a top annular portion over a bottom annular portion and define an annular step. The bottom annular portion can have a diameter greater than a diameter of the top annular portion. The hydrogel lens can include a relatively flat portion overlapping a center axis of the hydrogel lens. The hydrogel lens can include an annular opening configured to receive at least part of the media insert. The media insert can be removably attached to the hydrogel lens through an interference fit or through an adhesive fit. In some embodiments, the media insert can include one or more semiconductor devices and/or one or more energization elements.

In accordance with some embodiments, a method for removably attaching a media insert to a hydrogel lens includes receiving a first hydrogel lens including an annular opening, at least partially inserting a media insert into the annular opening of the first hydrogel lens, removing the media insert from the annular opening of the first hydrogel lens, receiving a second hydrogel lens including an annular opening, and at least partially inserting the removed media insert into the annular opening of the second hydrogel lens.

In some embodiments, the media insert can include an attachment mechanism. The attachment mechanism can include ribs at least partially along the circumference of the media insert or two or more tabs along the circumference of the media insert. The media insert can be formed of a material that is more rigid that a material used to form the first hydrogel lens and the second hydrogel lens.

Certain implementations of the hydrogel lens including the removable media insert have been outlined so that the detailed description below may be better understood. There are, of course, additional implementations that will be described below and which will form the subject matter of the claims.

In this respect, before explaining at least one implementation in detail, it is to be understood that the hydrogel lens including the removable media insert is not limited in its application to the details of construction and to the arrangements of the components set forth in the following description or illustrated in the drawings. Also, it is to be understood that the phraseology and terminology employed herein, as well as in the Abstract, are for the purpose of description and should not be regarded as limiting.

As such, those skilled in the art will appreciate that the conception upon which this disclosure is based may readily be utilized as a basis for the designing of other structures, methods, and systems for carrying out the several purposes of the hydrogel lens including the removable media insert. It is understood, therefore, that the claims include such equivalent constructions insofar as they do not depart from the spirit and scope of the present application.

BRIEF DESCRIPTION OF THE DRAWINGS

Like reference number indicate like elements throughout the detailed description and the drawings.

DETAILED DESCRIPTION

Figure 1:
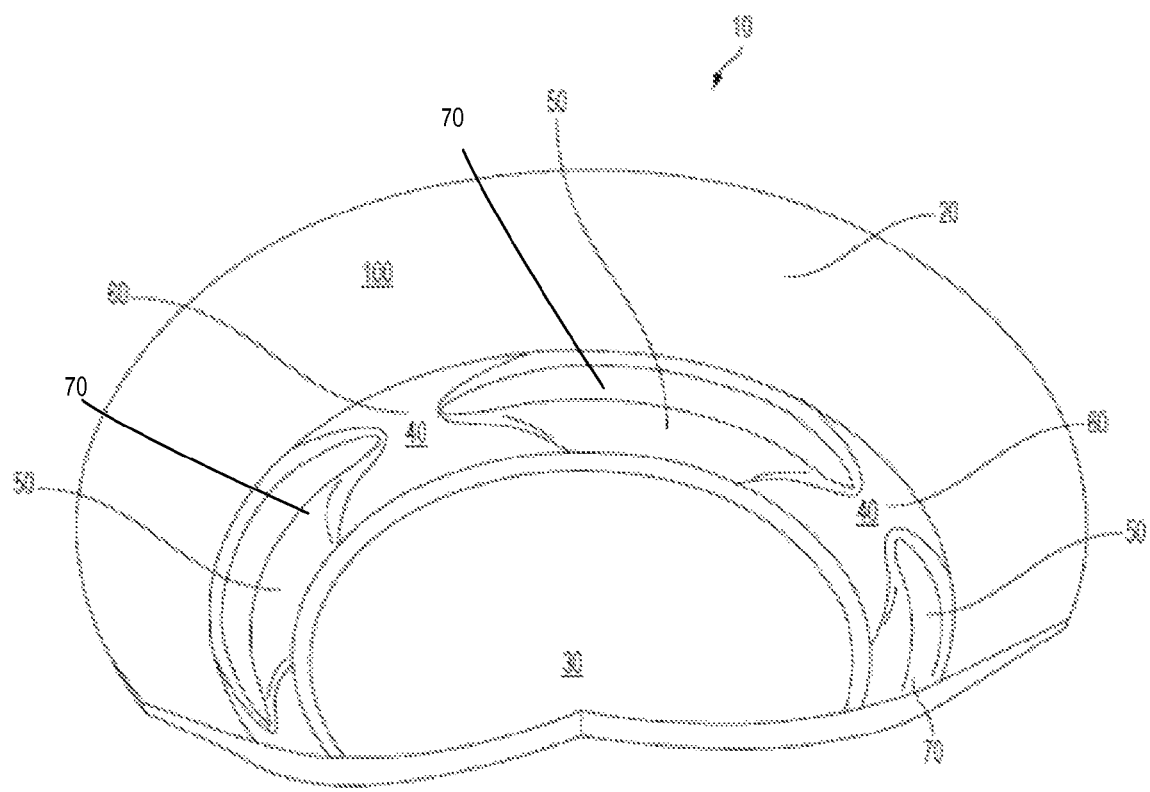
FIG. 1 illustrates a three-dimensional perspective view including a cross section of an exemplary ophthalmic device including raised portions.

A hydrogel lens including a removable media insert is disclosed. The removable media insert may be removably attached to the hydrogen lens using different attachment mechanisms. In addition, a raised portion that forms a cavity between an ocular surface and the hydrogel lens may be included in the hydrogel lens to improve oxygen transmission and tear flow between the ocular surface and the hydrogel lens.

GLOSSARY

In the description and the claims, various terms may be used for which the following definitions will apply:

Active Lens Insert: as used herein, may refer to an electronic or electromechanical insert device with controls based upon logic circuits.

Functionalized Layer Insert: as used herein, may refer to an insert for an ophthalmic device formed from multiple functional layers from which at least a portion of the multiple functional layers are stacked. The multiple layers may have unique functionality for each layer; or alternatively mixed functionality in multiple layers. In some embodiments, the layers can be rings.

Lens: as used herein, may refer to any ophthalmic device that resides in or on the eye.

Lens Components: as used herein, can include but are not limited to pigments, electrical components, UV blockers, tints, photoinitiators, catalysts, optical components, and/or active agents suitable to provide for specific functionality of a lens. Functionality may include, for example, one or more of: optical correction, enhanced vision, cosmetic effects, and therapeutic functionality.

Lens Design: as used herein, may refer to form, function and/or appearance of a desired Lens, which if fabricated, may provide functional characteristics comprising but not limited to optical power correction, color appearance, therapeutic functionality, wearability, acceptable permeability, shape, composition, conformability, acceptable lens fit (e.g., corneal coverage and movement), and acceptable lens rotation stability.

Media Insert: as used herein, may refer to a formable or rigid substrate capable of supporting an energization element, such as a battery, within an ophthalmic lens. In some embodiments, the media insert also includes one or more variable optic lenses.

Mold: as used herein, may refer to a rigid or semi-rigid object that may be used to form lenses from uncured formulations. Some molds can include one or two mold parts used to form a hydrogel lens comprising raised portions.

Ocular Insert: as used herein, may refer to any active lens insert, media insert, or functionalized layer insert that may be included within or attached to an ophthalmic device.

Ophthalmic Device: as used herein, may refer to any ophthalmic device that is capable of residing in or on the eye. These devices can provide one or more of: optical correction, therapy, and may be cosmetic. For example, the biomedical ophthalmic device can refer to an energized contact lens, intraocular lens, overlay lens, ocular insert, optical insert, punctal plug, or other similar ophthalmic device through which vision is corrected or modified, an eye condition is enhanced or prevented, and/or through which eye physiology is cosmetically enhanced (e.g., iris color). In some embodiments, the ophthalmic device of the invention can include soft contact lenses made from silicone elastomers or hydrogels, which include but are not limited to silicone hydrogels, and fluorohydrogels.

Ocular Surface: as used herein, may refer to the anterior surface area of the eye.

Optical Zone: as used herein, may refer to an area of an ophthalmic device or lens through which a wearer of the ophthalmic lens sees after the lens is formed.

Peripheral Zone: As used herein, the term "peripheral zone" or "non-optic zone" may refer to an area of an ophthalmic lens outside of the optic zone of the ophthalmic lens, and therefore outside of a portion of the ophthalmic lens through which a lens wearer sees while wearing the ophthalmic lens on, near or in the eye in a normally prescribed fashion.

Stacked: as used herein, can refer to the placement of at least two component surfaces in proximity to each other such that at least a portion of surface of one of a first component contacts at least a portion of a surface of a second component. In some embodiments, a film, whether for adhesion or other functions may reside between the two surfaces that are in proximity with each other. In some embodiments, the stacking of components may result in an encapsulated first component. The components can be an ocular insert and a hydrogel lens together forming an ophthalmic device.

Referring now to FIG. 1, a three-dimensional perspective view of an ophthalmic device 10 according to the present disclosure is provided. In particular, FIG. 1 shows an ophthalmic device 10 that includes exemplary raised portions 50 on the concave surface of the hydrogel lens 20 proximal to the ocular surface 100 of an eye. The ophthalmic device 10 includes a hydrogel lens 20. The hydrogel lens 20 includes an optic zone 30 and a peripheral zone 40. The hydrogel lens 20 may be composed of a silicon hydrogel or any biocompatible hydrogel material that is known to be used in ophthalmic lenses.

In some embodiments, for example, the ophthalmic lens type includes a silicone containing component. A silicone-containing component can be a component that contains at least one [—Si—O—] unit in a monomer, macromer or prepolymer. Preferably, the total amount of silicon (Si) and oxygen (O) present in the silicone-containing component is greater than about 20 weight percent, and more preferably greater than 30 weight percent of the total molecular weight of the silicone-containing component. Useful silicone-containing components preferably comprise polymerizable functional groups such as acrylate, methacrylate, acrylamide, methacrylamide, vinyl, N-vinyl lactam, N-vinylamide, and/or styryl functional groups.

The peripheral zone 40 of the hydrogel lens 20 can include a plurality of raised portions 50 on the inner surface of the hydrogel lens 20 proximal to the ocular surface 100. The raised portions 50 are spaced apart or positioned along the peripheral zone 40 and are not present in the optic zone 30. This is to ensure that the raised portions 50 do not interfere with the wearer's vision.

The raised portions 50 are spaced part along the peripheral zone 40 to create gap portions 60 between adjacent raised portions 50. FIG. 1 illustrates, for example, two gap portions 60. The gap portions 60 allow for oxygen transmission because the ocular surface 100 is exposed, i.e., not in contact with the hydrogel lens 20, in the gap portions 60 and oxygen can reach the ocular surface 100 without having to permeate through the raised portions 50. Tear flow may also occur in the gap portions 60, thereby further increasing the amount of oxygen provided to the ocular surface 100.

Two or more raised portions 50 may be included in the peripheral zone 40. The number and the size of the raised portions 50 will determine the number and size of gap portions 60, which can increase or decrease oxygen transmission and tear flow. For example, two or more gap portions 60 can be included in the peripheral zone 40 depending on the diameter of the hydrogel lens 20 and the circumferential length of the raised portions 50. In some embodiments, four raised portions can be included in the peripheral zone 40 and the gap portions 60 can have a circumferential length of about 1 mm.

In some embodiments, the raised portions 50 may be arranged to wrap around the peripheral zone 40 in a sinusoidal curve pattern. The amplitude of the sinusoidal curve may range between 3 microns to 80 microns. The number of peaks of the sinusoidal curve in the hydrogel lens 20 can range from, for example, two to 50. Other arrangements for the raised portions 50 are possible and the arrangements are not limited to sinusoidal curves or regular periodic geometry.

The raised portions 50 should have a surface area large enough so that the natural softness of the ocular surface 100 does not conform to the shape of the raised portions 50, thereby filling the cavities 70 between the ocular surface 100 and the raised portions 50. The raised portions 50 should not be so large, however, to cause high contact stress in the ocular surface 100 due to their relatively low flexibility, leading to discomfort or damage to the wearer.

The raised portions 50 may be composed of any biocompatible material previously described and/or that is known to be used in ophthalmic lenses. For example, in some embodiments, the raised portions 50 may be composed of hydrogel or silicon hydrogel. Accordingly, the raised portions 50 may be composed of the same hydrogel used to form the hydrogel lens 20. In yet other embodiments, the raised portions 50 may be composed of different materials that provide a more rigid material than the hydrogel lens 20. A more rigid material for the raised portions 50 can support the hydrogel lens 20 above the ocular surface 100.

In some embodiments, the hydrogel lens 20 and the raised portions 50 may be formed by cast molding. A mold may be used to form the hydrogel lens 20 and the raised portions 50 from uncured formulations. Some molds may include two mold parts forming a hydrogel lens 20 and the raised portions 50. It is possible to achieve different properties for the hydrogel lens 20 and the raised portions 50 by selectively polymerizing the raised portions 50 for a longer period of time or by using a different monomer. This may result in the raised portions 50 having increased rigidity, stiffness, and/or strength.

Figure 2:
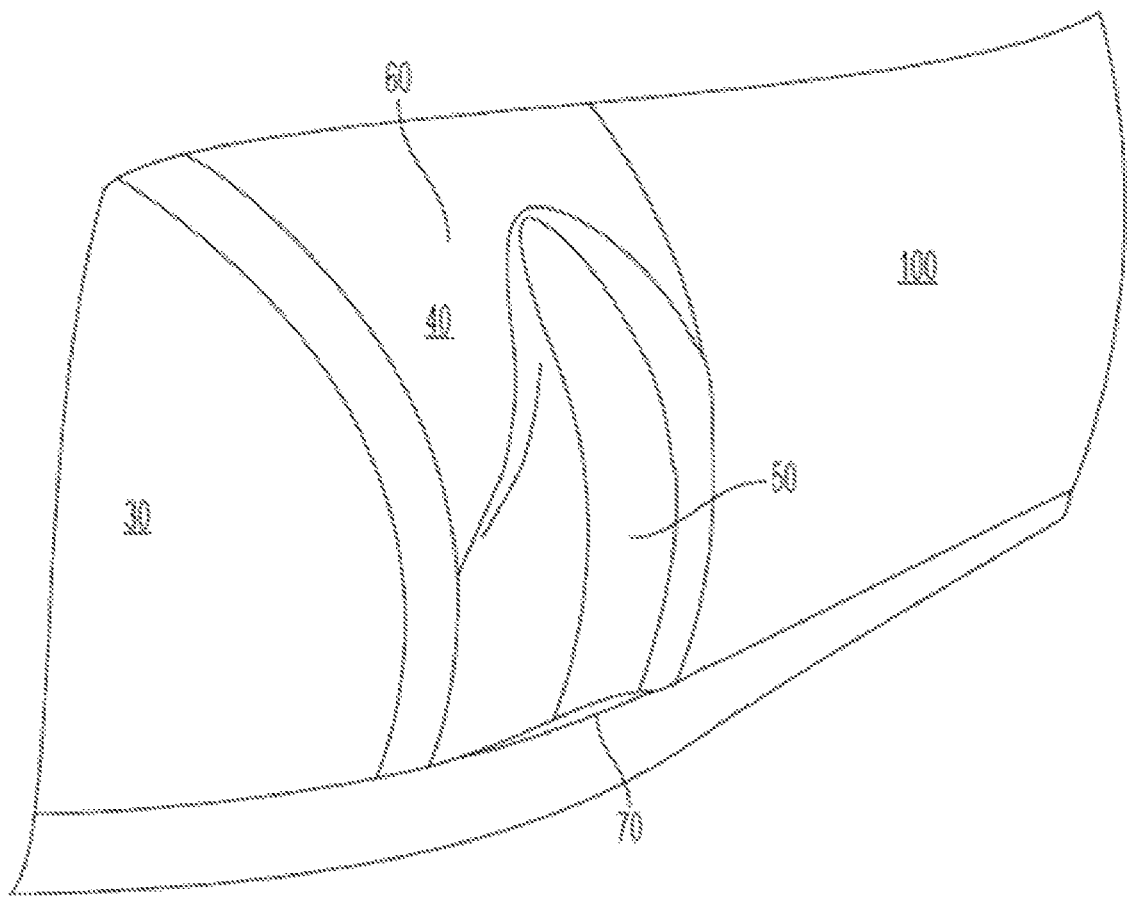
FIG. 2 illustrates a partial enlarged perspective view and cross section of the raised portion of an exemplary hydrogel lens including raised portions.

Referring now to FIG. 2, an enlarged perspective view of the raised portion 50 of a hydrogel lens 20 is shown. The raised portion 50 transitions smoothly along the peripheral zone 40 of the hydrogel lens 20 in both radial and tangential directions. The size and shape of the raised portion 50 can be designed in accordance with the size and shape of the hydrogel lens 20.

The raised portions 50 of the hydrogel lens 20 can create cavities 70 between the hydrogel lens 20 and the ocular surface 100. In some embodiments, the cavities 70 can have a thickness of at least 10% of the thickness of the hydrogel lens 20. For example, in some embodiments, the cavities 70 can be about 0.065 mm above the ocular surface 100. Therefore, the raised portions 50 prevent the hydrogel lens 20 from adhering to the ocular surface 100 and allow for oxygen transmission and tear flow inside the cavity 70.

The size and geometry of the cavities 70 are determined by the number and geometry of the raised portions 50. The larger the size and geometry of the cavities 70, the greater the surface area of the ocular surface 100 that is not in contact with the hydrogel lens 20 and, therefore, the greater the oxygen transmission and tear flow. If the surface area and the number of raised portions 50 are too high, however, oxygen transmission and tear flow to the ocular surface 100 may be limited. Therefore, the size and number of the raised portions 50 should be selected to maximize oxygen transmission and tear flow to promote eye health. As such, in some embodiments, the raised portions 50 have a total surface area that is less than 50% of the surface area of the ocular surface 100.

Figure 3:
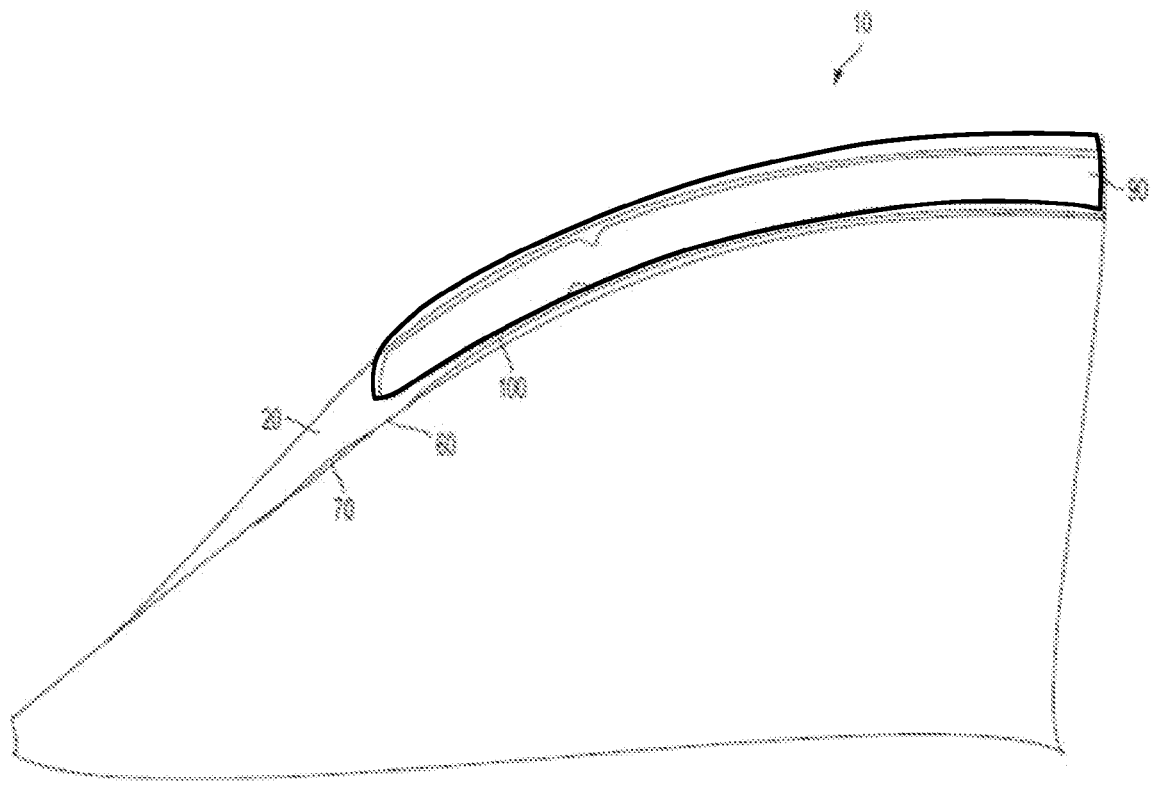
FIG. 3 illustrates a partial cross-sectional view of an exemplary ophthalmic device including raised portions and a removable media insert.

Referring to FIG. 3, by improving oxygen transmission and tear flow, the hydrogel lens 20 enables the incorporation of components, such as active lens inserts, media inserts, and functionalized layer inserts onto the hydrogel lens 20. The components may have lower oxygen permeability relative to hydrogel lens 20. In some embodiments, the components may be stacked over one another. For example, as shown in FIG. 3, the removable media insert 90 is attached to the hydrogel lens 20, which supports the removable media insert 90. As illustrated by the cross-sectional view in FIG. 3, the removable media insert 90 can extend above the top surface of the hydrogel lens 20 opposite the ocular surface 100. The raised portions 50 cannot be seen in the cross-sectional view of the ophthalmic device 10 in FIG. 3. Because the hydrogel lens 402 can include raised portions 50, the removable media insert 90 may be used without adversely affecting oxygen transmission and tear flow in the eye.

Because the removable media insert 90 may be rigid, the removable media insert 90 forms a nearly unbreakable seal with the ocular surface 100. As such, as opposed to being arranged in the peripheral zone 40, the raised portions 50 may be arranged along the circumference of the removable media insert 90, such that the raised portions 50 extend radially inward and outward enough to smoothly blend into the surface of the hydrogel lens 20 and minimize contact stress with the eye.

Figure 4A:
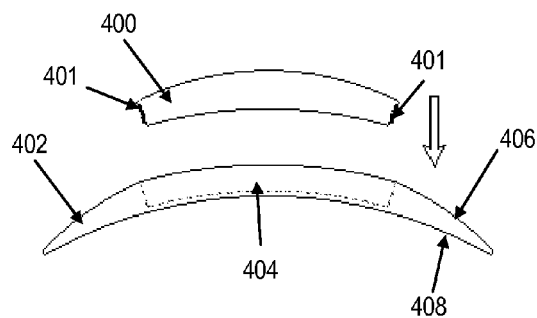
FIG. 4a illustrates a partial cross-sectional view of an exemplary ophthalmic device and a separate removable media insert with a first exemplary attachment mechanism.

Referring to FIG. 4a, an ophthalmic device may include a removable media insert 400 incorporating electronic components, such as semiconductor devices and energization elements. In some embodiments, the media insert 400 may include an optical zone portion providing an optical property, such as those utilized for vision correction, and a non-optical zone portion. An energization element can be placed on one or both of the optic zone portion and the non-optical zone portion of the media insert 400. The removable media insert 400 can be an annular insert that is either rigid or flexible and can circumvent an optical zone through which a wearer sees. Therefore, in some embodiments, the media insert 400 can have a radius substantially equal to or smaller than the radius of the optic zone 30.

Figure 4C:
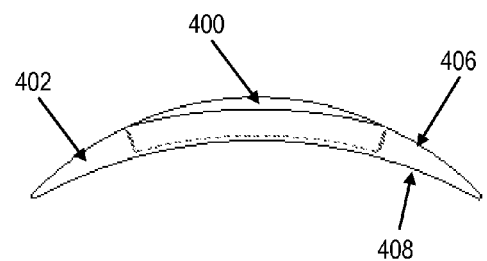
FIG. 4c illustrates a partial cross-sectional view of an exemplary ophthalmic device including the removable media insert with the first exemplary attachment mechanism.
Figure 4B:
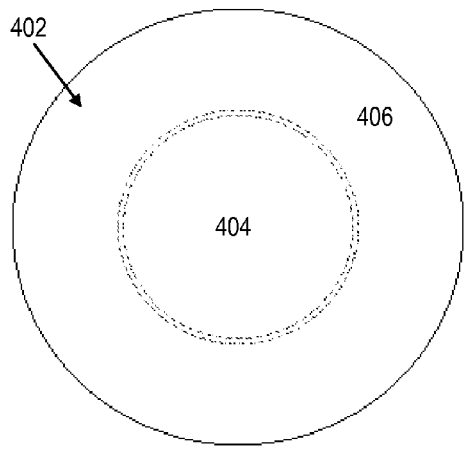
FIG. 4b illustrates a top view of the exemplary ophthalmic device without the removable media insert.

The media insert 400 can be removably attached to a hydrogel lens 402 within an annular opening 404 formed on an outer surface 406 of the hydrogel lens 402. An inner surface 408 of the hydrogel lens 402 is opposed to the outer surface 406 and is in contact with the ocular surface 100 when the hydrogel lens 402 is worn. The annular opening 404 does not extend through the inner surface 408 of the hydrogel lens 402. In some embodiments, the hydrogel lens 402 may be the hydrogel lens 20 that includes the raised portions 50 in its peripheral zone 40. In other embodiments, as shown in the top view of FIG. 4b, the hydrogel lens 402 may not include raised portions 50.

Figure 4D:
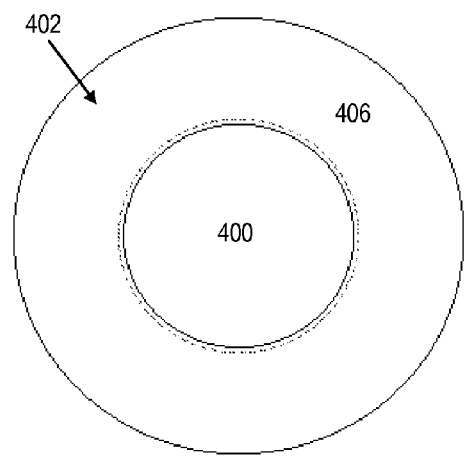
FIG. 4d illustrates a top view of the exemplary ophthalmic device including the removable media insert.

The media insert 400 includes ribs 401 located along at least part of the circumference of the media insert 400. The ribs 401 include a series of protrusions extending from the circumferential wall of the media insert 400. The ribs 401 can be made of the same material as the media insert 400 or can be made from another material that is rigid. Because the hydrogel lens 402 is made of a flexible material, the protrusions of the ribs 401 apply a friction force to the walls of the annular opening 404, thereby removably attaching the media insert 400 to the hydrogel lens 402. In some embodiments, as show in the cross-section of FIG. 4c, an upper surface of the media insert 400 may partially protrude from the outer surface 406 of the hydrogel lens 402. In other embodiments, the upper surface of the media insert 400 may be flush with the outer surface 406 of the hydrogel lens 402. FIG. 4d illustrates a top-view of the hydrogel lens 402 with the inserted media insert 400.

Because the media insert 400 is removably attached to the hydrogel lens 402, it may be removed from the hydrogel lens 402 for insertion into, for example, another hydrogel lens 402. As such, the hydrogel lens 402 may be disposed by a wearer while the media insert 400 is maintained for removable attachment to another hydrogel lens 402.

Figure 5A:
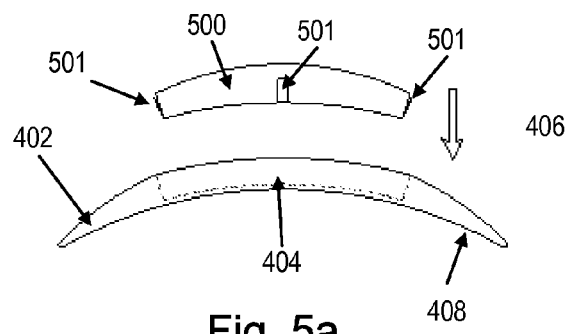
FIG. 5a illustrates a partial cross-sectional view of an exemplary ophthalmic device and a separate removable media insert with a second exemplary attachment mechanism.

Referring to FIG. 5a, an ophthalmic device may include a removable media insert 500. The media insert 500 may incorporate the same electronic components as the removable media insert 400. The media insert 500 can be removably attached to the hydrogel lens 402 within the annular opening 404. The media insert 500 includes tabs 501 located along the circumference of the media insert 500. The media insert 500 may include any number of two or more tabs 501 that can be strips or wires extending radially from the media insert 500. In some embodiments, preferably, the tabs 501 can be equidistantly separated along the circumference of the media insert 500, while in other embodiments, the tabs 501 may not be equidistantly separated. The tabs 501 can be made of the same material as the media insert 500 or can be made of another material that is resilient to allow the tabs 501 to flex as they are inserted in the annular opening 404 and to return to their unstressed configuration when in the annular opening 404.

Figure 5C:
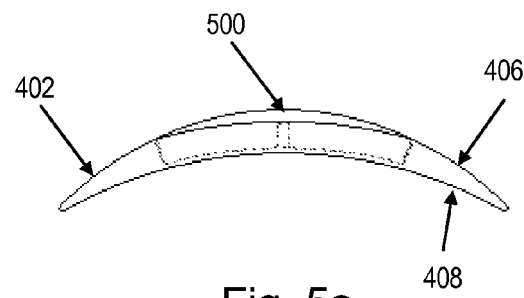
FIG. 5c illustrates a partial cross-sectional view of an exemplary ophthalmic device including the removable media insert with the second exemplary attachment mechanism.
Figure 5B:
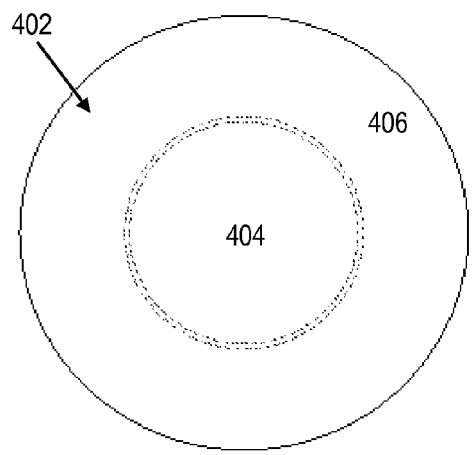
FIG. 5b illustrates a top view of the exemplary ophthalmic device without the removable media insert.
Figure 5D:
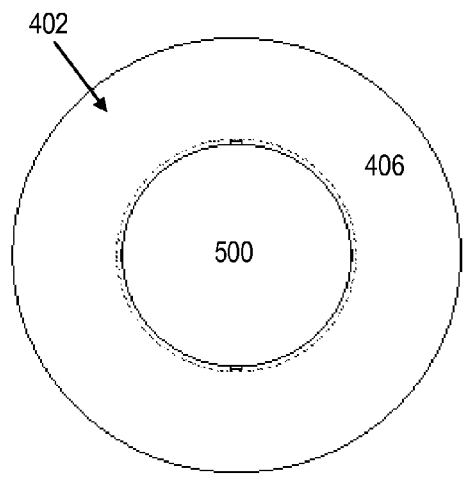
FIG. 5d illustrates a top view of the exemplary ophthalmic device including the removable media insert.

The resilient material of the tabs 501 will initially flex inwards toward the circumference of the media insert 500 as the tabs 501 come in contact with the wall of the annular opening 404. Once the media insert 500 is inserted into the annular opening 404, the tabs 501 return to their unstressed configuration and the force applied by the resilient material of the tabs 501 to the walls of the annular opening 404 removably attaches the media insert 500 to the hydrogel lens 402. In some embodiments, as show in the cross-section of FIG. 5c, an upper surface of the media insert 500 may partially protrude from the outer surface 406 of the hydrogel lens 402. In other embodiments, the upper surface of the media insert 500 may be flush with the outer surface 406 of the hydrogel lens 402. FIG. 5d illustrates a top-view of the hydrogel lens 402 with the inserted media insert 500. Because the media insert 500 is removably attached to the hydrogel lens 402, it may be removed from the hydrogel lens 402 for insertion into, for example, another hydrogel lens 402.

Figure 6A:
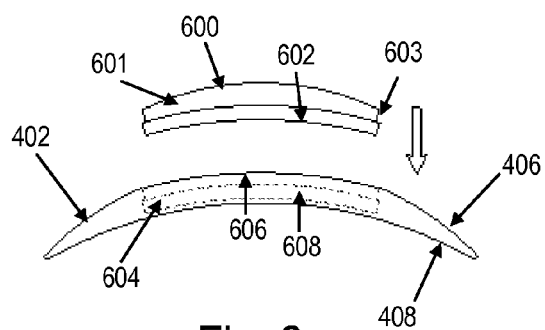
FIG. 6a illustrates a partial cross-sectional view of an exemplary ophthalmic device and a separate removable media insert with a third exemplary attachment mechanism.

Referring to FIG. 6a, an ophthalmic device may include a removable media insert 600. The media insert 600 may incorporate the same electronic components as the media insert 400. The media insert 600 can be removably attached to the hydrogel lens 402 within the annular opening 604. The media insert 600 can be a functionalized layer insert and include a top annular portion 601 and a bottom annular portion 602 in a stacked configuration that define the annular step 603. The bottom annular portion 602 has a greater diameter that the top annular portion 601. The stacked configuration of the media insert 600 can allow for incorporation of electronic components that may require a stacked layout. The annular opening 604 includes a top annular region 606 and a bottom annular region 608. Similarly, the bottom annular region 608 has a greater diameter than the top annular region 606.

Figure 6C:
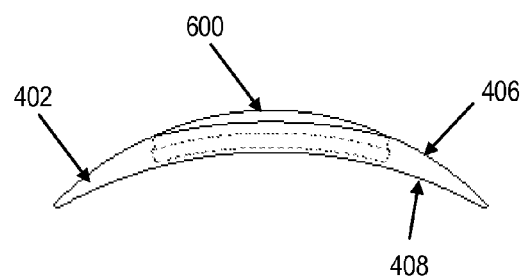
FIG. 6c illustrates a partial cross-sectional view of an exemplary ophthalmic device including the removable media insert with the third exemplary attachment mechanism.
Figure 6B:
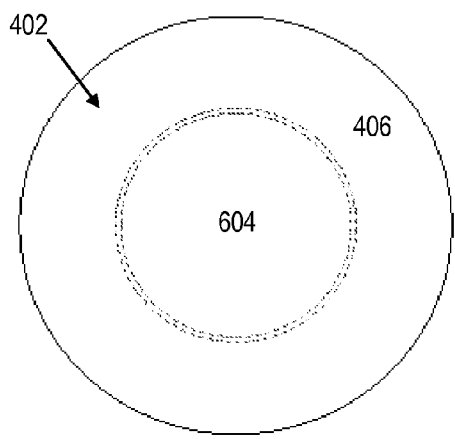
FIG. 6b illustrates a top view of the exemplary ophthalmic device without the removable media insert.
Figure 6D:
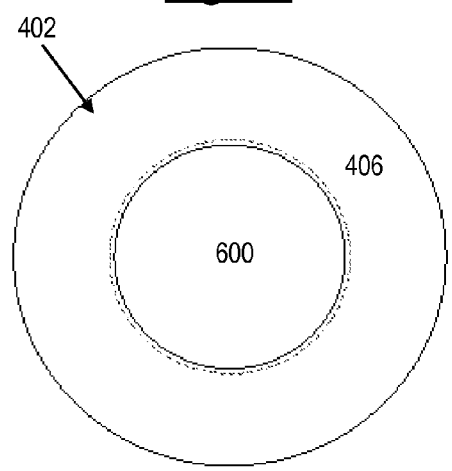
FIG. 6d illustrates a top view of the exemplary ophthalmic device including the removable media insert.

As the media insert 600 comes in contact with the top annular region 606 of the annular opening 604, it will cause the flexible walls if the top annular region 606 to flex radially outward. Once the media insert 600 is inserted into the annular opening 604, the flexible walls of the top annular region 606 will return to their unstressed position and cover the top of the annular step 603. The force applied by the hydrogel lens 402 to the annular step 603 removably attaches the media insert 600 to the hydrogel lens 402 through an interference fit. In some embodiments, as show in the cross-section of FIG. 6c, an upper surface of the media insert 600 may partially protrude from the outer surface 406 of the hydrogel lens 402. In other embodiments, the upper surface of the media insert 600 may be flush with the outer surface 406 of the hydrogel lens 402. FIG. 6d illustrates a top-view of the hydrogel lens 402 with the inserted media insert 600. Because the media insert 600 is removably attached to the hydrogel lens 402, it may be removed from the hydrogel lens 402 for insertion into, for example, another hydrogel lens 402.

Figure 7A:
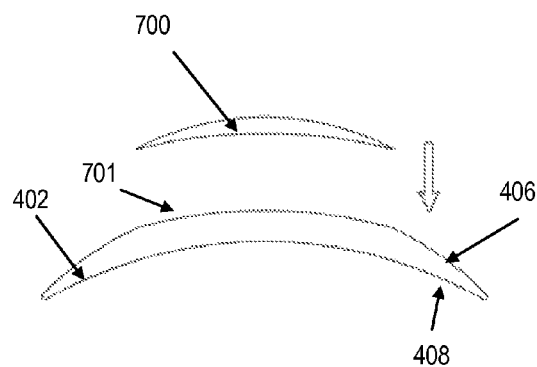
FIG. 7a illustrates a partial cross-sectional view of an exemplary ophthalmic device and a separate removable media insert with a fourth exemplary attachment mechanism.
Figure 7C:
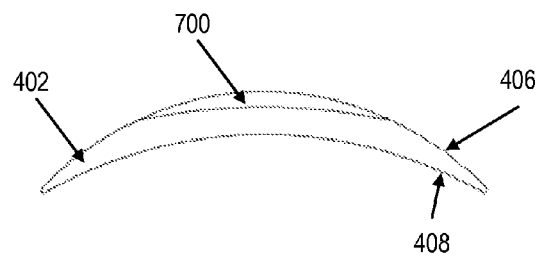
FIG. 7c illustrates a partial cross-sectional view of an exemplary ophthalmic device including the removable media insert with the fourth exemplary attachment mechanism.
Figure 7B:
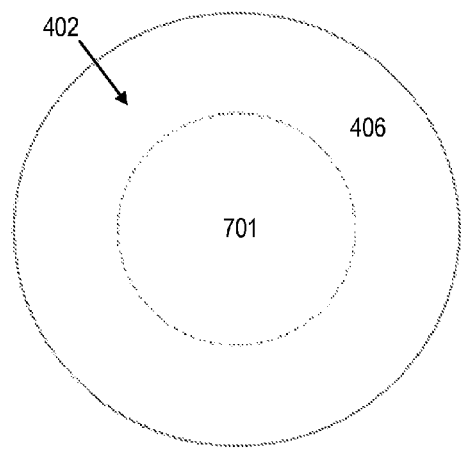
FIG. 7b illustrates a top view of the exemplary ophthalmic device without the removable media insert.
Figure 7D:
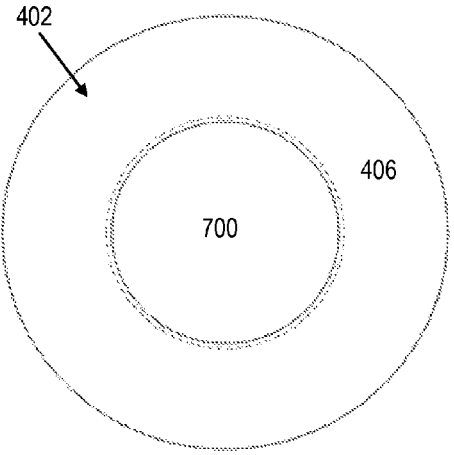
FIG. 7d illustrates a top view of the exemplary ophthalmic device including the removable media insert.

Referring to FIG. 7a, an ophthalmic device may include a removable media insert 700. The media insert 700 may incorporate the same electronic components as the media insert 400. The media insert 700 can be removably attached to a relatively flat region 701 of the outer surface 406 of the hydrogel lens 402. The relatively flat region 701 can have a smaller slope relative to the rest of the hydrogel lens 402. As the media insert 700 comes in contact with the relatively flat region 701, an adhesive force, such as surface tension, removably attaches the media insert 700 to the outer surface 406 of the hydrogel lens 402. As shown in the cross-section of FIG. 7c, the media insert 700 completely protrudes from the outer surface 406 of the hydrogel lens 402. FIG. 7d illustrates a top-view of the hydrogel lens 402 with the inserted media insert 700. Because the media insert 700 is removably attached to the hydrogel lens 402, it may be removed from the hydrogel lens 402 for insertion into, for example, another hydrogel lens 402.

Additional features, advantages, and aspects of the disclosure may be set forth or apparent from consideration of the following detailed description, drawings, and claims. Moreover, it is to be understood that both the foregoing summary of the disclosure and the following detailed description are exemplary and intended to provide further explanation without limiting the scope of the disclosure as claimed.

What is claimed is:

1. An ophthalmic device comprising:
    a hydrogel lens comprising an optic zone and a peripheral zone that is outside of the optic zone;
    two or more raised portions in the peripheral zone of the hydrogel lens; and
    a media insert removably attached within the optic zone of the hydrogel lens.

2. The ophthalmic device of claim 1, wherein gap portions are located in between the raised portions and allow for oxygen transmission and tear flow.

3. The ophthalmic device of claim 1, wherein an upper surface of the media insert partially protrudes from an outer surface of the hydrogel lens.

4. The ophthalmic device of claim 1, wherein the media insert comprises one or more semiconductor devices.

5. The ophthalmic device of claim 1, wherein the media insert further comprises one or more energization elements.

6. An ophthalmic device comprising:
    a hydrogel lens comprising a relatively flat portion overlapping a center axis of the hydrogel lens; and
    a media insert removably attached to the hydrogel lens.

7. The ophthalmic device of claim 6, wherein the media insert is removably attached to the hydrogel lens through an adhesive fit.

8. An ophthalmic device comprising:
    a hydrogel lens comprising an annular opening configured to receive at least part of a media insert; and
    a media insert removably attached within the annular opening of the hydrogel lens.

9. The ophthalmic device of claim 8, wherein the media insert comprises ribs at least partially along its circumference.

10. The ophthalmic device of claim 8, wherein the media insert comprises two or more tabs along its circumference.

11. The ophthalmic device of claim 10, wherein the tabs are made of a resilient material.

12. The ophthalmic device of claim 8, wherein the media insert comprises a top annular portion over a bottom annular portion and define an annular step, wherein the bottom annular portion has a diameter greater than a diameter of the top annular portion.

13. The ophthalmic device of claim 8, wherein the media insert is removably attached to the hydrogel lens through an interference fit.

14. A method for removably attaching a media insert to a hydrogel lens, the method comprising:
    receiving a first hydrogel lens including an annular opening;
    at least partially inserting a media insert into the annular opening of the first hydrogel lens;
    removing the media insert from the annular opening of the first hydrogel lens;
    receiving a second hydrogel lens including an annular opening; and
    at least partially inserting the removed media insert into the annular opening of the second hydrogel lens.

15. The method of claim 14, wherein the media insert comprises an attachment mechanism.

16. The method of claim 15, wherein the attachment mechanism comprises ribs at least partially along the circumference of the media insert.

17. The method of claim 15, wherein the attachment mechanism comprises two or more tabs along the circumference of the media insert.

18. The method of claim 14, wherein the media insert is formed of a material that is more rigid than a material used to form the first hydrogel lens and the second hydrogel lens.

* * * * *